United States Patent
Wary et al.

(10) Patent No.: US 8,137,968 B2
(45) Date of Patent: Mar. 20, 2012

(54) SELECTED ENDOTHELIAL PROGENITOR CELLS AND METHODS FOR USE

(75) Inventors: Kishore K. Wary, Elmhurst, IL (US); Yidan Zhao, Chicago, IL (US); Asrar B. Malik, Hinsdale, IL (US); You-Yang Zhao, Grayslake, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 455 days.

(21) Appl. No.: 12/038,020

(22) Filed: Feb. 27, 2008

(65) Prior Publication Data
US 2008/0206200 A1 Aug. 28, 2008

Related U.S. Application Data

(60) Provisional application No. 60/904,335, filed on Feb. 28, 2007, provisional application No. 60/920,412, filed on Mar. 28, 2007, provisional application No. 60/976,828, filed on Oct. 2, 2007.

(51) Int. Cl.
*C12N 5/00* (2006.01)
*C12N 5/02* (2006.01)
*C12N 5/07* (2010.01)
*C12N 5/10* (2006.01)

(52) U.S. Cl. ........ 435/377; 435/325; 435/372; 435/355; 424/93.1

(58) Field of Classification Search .................... 435/377
See application file for complete search history.

(56) References Cited

U.S. PATENT DOCUMENTS

| 5,980,887 A | 11/1999 | Isner et al. ................... 424/93.7 |
| 7,794,705 B2 | 9/2010 | Pecora et al. .................. 424/93.7 |
| 2004/0001807 A1* | 1/2004 | Edelberg et al. ............ 424/93.7 |

OTHER PUBLICATIONS

Kalka et al, PNAS, 2000;97:3422-3427.*
Asahara et al., "Isolation of putative progenitor endothelial cells for angiogenesis", Science 1997 275:964-967.
Murohara et al., "Nitric oxide synthase modulates angiogenesis in response to tissue ischemia", J. Clin. Invest. 1998 101(11):2567-2578.
Gargett et al., "Isolation, characterization and long-term culture of human myometrial microvascular endothelial cells", Human Reproduction 2000 15(2):293-301.
Reyes et al., "Origin of endothelial progenitors in human postnatal bone marrow", J. Clin. Invest. 2002 109:337-346.
Gehling et al., "In vitro differentiation of endothelial cells from AC133-positive progenitor cells", Blood 2000 95:3106-3112.
Brugger et al., "Positively selected autologous blood CD34' cells and useparated peripheral blood progenitor cells mediate identical hematopoietic engraftment after high-dose VP16, ifosfamide, carboplatin, and epirubicin", Blood 1994 84(5):1421-1426.
Quirici et al., "Differentiation and expansion of endothelial cells from human bone marrow CD133+cells", British Journal of Haematology 2001 115:186-194.
Vasa et al., "Increase in circulating endothelial progenitor cells by statin therapy in patients with stable coronary artery disease", Circulation 2001 103:2885-2890.
Shi et al., "Evidence for circulating bone marrow-derived endothelial cells", Blood 1998 92(2):362-367.
Kawamoto et al., "Therapeutic potential of Ex Vivo expanded endothelial progenitor cells for myocardial ischemia", circulation 2001 103:634-637.
Wary et al., "A requirement for caveolin-1 and associated kinase fyn in integrin signaling and anchorage-dependent cell growth", Cell 1998 94:625-634.
Wary et al., "Analysis of VEGF-responsive genes inveolved in the activation of endothelial cells", Molecular Cancer 2003 2:25 pp. 1-12.
Chavakis et al., "Role of β2-integrins for homing and neovascularizatiobn capacity of endothelial progenitor cells", JEM 2005 201(1):63-72.

* cited by examiner

*Primary Examiner* — Valarie Bertoglio
(74) *Attorney, Agent, or Firm* — Licata & Tyrrell P.C.

(57) ABSTRACT

The present invention is a method for preparing a substantially pure population of endothelial progenitor cells wherein said cells express Flk-1, CD34, $\alpha_5\beta_1$ integrin fibronectin, and vWF and exhibit an adherent phenotype and methods for using the same to decrease the severity of lung injury, prevent pulmonary edema, restore endothelial barrier function, induce productive wound healing and angiogenesis, and increase survival rate in acute lung injury (ALI).

2 Claims, 2 Drawing Sheets

SELECTED ENDOTHELIAL PROGENITOR CELLS AND METHODS FOR USE

This application claims benefit of priority to U.S. Provisional Patent Application Ser. Nos. 60/904,335, filed Feb. 28, 2007; 60/920,412, filed Mar. 28, 2007; and 60/976,828, filed Oct. 2, 2007, the contents of which are incorporated herein by reference in their entireties.

This invention was made with government support under Grant Nos. R01 HL 45638, P01 HL 60678, P01 HL 77806, T32 HL 07829, and R01 HL 07935 awarded by the National Institutes of Health. The government has certain rights in the invention.

BACKGROUND OF THE INVENTION

Acute lung injury (ALI) is a complex multi-factorial syndrome which manifests as leaky lung microvessels, protein-rich alveolar edema, and hypoxemia that is intractable to ventilation with high levels of oxygen. The patients are often septic, and at present, only different modes of ventilator therapy are used for their clinical management. Most therapeutic modalities, including extracorporeal oxygenation, corticosteroids, prostaglandins, surfactant, and nitric oxide, generally fail to improve outcome (Fulkerson, et al. (1996) *Arch. Intern. Med.* 156: 29-38). The pathophysiology of ALI remains unclear. However, a common finding is the recruitment and activation of inflammatory cells into the lung (Brennan, et al. (1995) *Br. Med. Bull.* 51: 368-384; Rahman & MacNee (1995) *Thorax* 51:348-350). Airway epithelial cells have also been shown to act as immune effectors by secreting proinflammatory mediators (Thompson, et al. (1995) *Eur. Respir.* 8: 127-149). Once triggered, the inflammatory response results in lung inflammation, neutrophils sequestration in lungs, and increased microvascular permeability leading to plasma leakage into lung tissue and excessive fluid accumulation in airspaces. Prognosis of these critically ill patients is typically poor with mortality ranging from 50% to 60% among the 150,000 to 180,000 patients diagnosed annually, which is more fatal than breast tumor and HIV/AIDS disease combined (Ware & Matthay (2005) *NEJM* 353: 2788-96). At present ventilator therapy is used for their clinical management. Unfortunately, there are no conventional therapies available to restore the integrity of the microvascular endothelial barrier (the key underlying factor in edema formation), thereby preventing the accumulation of protein-rich fluid in the extravascular space and promoting productive wound healing.

SUMMARY OF THE INVENTION

The present invention is a method for preparing a substantially pure population of endothelial progenitor cells (EPCs). The method involves culturing isolated mononuclear cells in the absence of epidermal growth factor (EGF) and presence of vascular endothelial growth factor-121 (VEGF$^{121}$) and vascular endothelial growth factor-165 (VEGF$^{165}$) to induce expansion of adherent endothelial progenitor cells; and selecting for adherent endothelial progenitor cells, wherein said cells express fetal liver kinase 1 (Flk-1) and CD34. Isolated populations of adherent endothelial progenitor cells are provided as are methods for using such cells to promote wound healing and angiogenesis, decrease the severity of lung injury, prevent pulmonary edema, and increase survival rate in acute lung injury.

BRIEF DESCRIPTION OF THE DRAWINGS

FIG. 2 shows that mouse-EPCs (mEPCs) treatment promotes increased survival and decreased lung edema following LPS challenge.

DETAILED DESCRIPTION OF THE INVENTION

It has now been found that selected EPCs, which express a subset of integrins, fibronectin and vWF, can reduce the severity of lung injury, reduce pulmonary edema, and increase survival rate in a model of ALI. Such an effect was not achieved with mature endothelial cells. Specifically, EPCs prepared herein were found to robustly synthesize and deposit fibronectin in the matrix and abundantly express $\alpha_4\beta_1$ and $\alpha_5\beta_1$ integrins to promote EPC attachment to fibronectin, thereby facilitating the spreading and reannealing of the endothelial barrier. Moreover, the present EPCs promoted adherens junction assembly in endothelial cells, formed focal adhesion sites in association with tyrosine phosphorylation of FAK, induced the rapid activation of RhoA in endothelial cells, and delayed activation of Rac1, consistent with retraction of endothelial cells followed by barrier resealing. Accordingly, the present invention provides a method for preparing these selected EPCs and methods for using the same to decrease severity of lung injury, prevent pulmonary edema, promote productive wound healing and angiogenesis, and increase survival rate in acute lung injury.

In accordance with the present invention, a substantially pure population of endothelial progenitor cells is prepared by culturing isolated mononuclear cells in the absence of epidermal growth factor and presence of vascular endothelial growth factor-121 and vascular endothelial growth factor-165 to induce expansion of adherent endothelial progenitor cells; and selecting adherent cells which express fetal liver kinase 1 (Flk-1) and CD34 thereby preparing a substantially pure population of endothelial progenitor cells.

The term "progenitor cell", which is distinct from a stem cell, is used herein to describe a cell that gives rise to progeny in a defined cell lineage. An "endothelial progenitor cell" is a cell that gives rise to cells of the endothelium. The endothelium is the thin layer of cells that line the interior surface of blood vessels, forming an interface between circulating blood in the lumen and the rest of the vessel wall. Endothelial cells line the entire circulatory system, from the heart to the smallest capillary. These cells reduce friction of the flow of blood allowing the fluid to be pumped further. As used herein, a "substantially pure" population of endothelial progenitor cells is a population of cells that is composed of at least about 80% to 85% endothelial progenitor cells, preferably at least about 90%, and even more preferably about 95% or more endothelial progenitor cells.

The method begins with culturing isolated mononuclear cells. As is conventional in the art, the term "mononuclear cell" is a general term for cells having a nucleus therein, and specific examples thereof are lymphocytes (T cells, B cells and NK cells), monocytes, hematopoietic stem cells, myelocytes, blast cells, etc. Mononuclear cells can be isolated from any suitable source including, e.g., bone marrow, blood, or spleen, from any suitable donor, e.g., a human, a non-human primate, a pig, a sheep, a cow, a rodent or the like. In particular embodiments, mononuclear cells are isolated from bone marrow. In this regard, cells of the invention are described as "bone marrow-derived." In so far as cells of the invention find application in the treatment of human disease, it is particularly desirable that the cells are isolated from a human donor. Methods of obtaining mononuclear cells from blood or bone marrow, such as differential sedimentation through an appropriate medium, e.g., FICOLL-HYPAQUE (Pharmacia Biotech, Uppsala, Sweden), are well-known and suitable for use in this invention. Alternatively, CD34+ cells can be isolated using an anti-CD34 monoclonal antibody, in particular, by flow cytometry (FACS) or by magnetic beads that are coated with specific antibodies or tissue culture dishes coated with specific antibodies.

In accordance with the method of the invention, culturing of isolated mononuclear cells is carried out in culture medium. In one embodiment, the cells are cultured on a solid substrate that permits the adhesion of a subpopulation of cells. In another embodiment, the solid substrate is a container, such as a tissue culture dish. In a further embodiment, the solid substrate is in the form of beads designed for tissue culture. In accordance with such embodiments, it is particularly desirable that the solid substrate is coated with gelatin. The medium used for culturing cells of the invention can be a growth medium or any buffer that maintains the viability of the cells. A variety of culture media are known and are suitable for use. Desirably, the culture medium is a "defined medium" which refers to a medium composed of nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: all essential amino acids, and usually the basic set of twenty amino acids; an energy source, usually in the form of a carbohydrate such as glucose; vitamins and/or other organic compounds required at low concentrations; free fatty acids; and trace elements, where trace elements are defined as inorganic compounds or naturally occurring elements that are typically required at very low concentrations, usually in the micromolar range. In particular embodiments, the defined medium is an endothelial growth medium such as EGM-2 or EGM-2MV.

The defined medium can also be supplemented with serum. Specific, non-limiting examples of serum are horse, calf or fetal bovine serum. The medium can have between about 3% by volume to about 10% by volume serum, or desirably about 5% by volume of added serum.

In certain embodiments, the defined medium contains one or more additional additives. Specific, non-limiting examples of these additives include hydrocortisone, heparin, ascorbic acid, L-glutamine and antimicrobial agents such as gentamycin and amphotericin-B.

To specifically expand the subpopulation of adherent endothelial progenitor cells of the present invention, a particular combination of growth factors are added to the growth medium. As is conventional in the art, a growth factor is a substance that promotes cell growth, survival, and/or differentiation. In general, growth factors stimulate cell proliferation or maturation when they bind to their receptor. A growth factor can be a naturally occurring factor or a factor synthesized using recombinant protein production methodologies. In particular, two specific vascular endothelial growth factor (VEGF) isoforms, namely VEGF$^{165}$ and VEGF$^{121}$ were found to enhance the ex vivo propagation and expansion of adherent EPCs, which synthesized $\alpha_5\beta_1$ integrin, and deposited fibronectin and von Willebrand Factor (vWF). Accordingly, specific embodiments provide for the addition of VEGF$^{165}$ and VEGF$^{121}$ to the culture medium. In one embodiment, the culture medium contains a final concentration of 50 ng/ml of each VEGF isoform. In addition to VEGF, the culture medium desirably also contains basic fibroblast growth factor (bFGF), heparin and Insulin-like Growth Factor-I (IGF-I). Moreover, particular embodiments specifically exclude the addition of epidermal growth factor (EGF) to the culture medium.

Culturing, which includes expansion and selection, of the endothelial progenitor cells of the invention is desirably carried out under "standard incubation conditions," which refers to the physicochemical conditions in an incubator designed for tissue culture in which cells are placed. Generally, standard incubation conditions are about 37 degrees Celsius and about 5% $CO_2$ content with humidification. All tissue culture techniques and equipment should be performed under sterile conditions.

After the cells have been cultured for a sufficient time, desirably about 6 to 7 days, adherent endothelial progenitor cells are selected, e.g., by removing non-adherent cells from the culture. This can be achieved by removing culture medium which contains the non-adherent cells. As disclosed herein, endothelial progenitor cells of the invention adhere based upon the expression of $\alpha_5\beta_1$ integrin, fibronectin, and vWF. Accordingly, in so far as the cells of the invention are selected for being adherent, so too are these cells being selected for expression of $\alpha_5\beta_1$ integrin, fibronectin and vWF. Adherent endothelial cells, i.e., cells remaining attached to the solid substrate are then allowed to further expand, e.g., for an addition 12 to 14 days. After a total of approximately 18 to 21 days, a substantially pure population of endothelial progenitor cells is produced. The purity of the cells can be assessed by expression of endothelial progenitor cell markers.

A cell marker is a protein, glycoprotein, or other molecule expressed by a cell, which serves to help identify the cell. A cell marker can generally be detected by conventional methods. Specific, non-limiting examples of methods for detection of a cell surface marker are immunohistochemistry, fluorescence activated cell sorting (FACS), magnetic antibody cell separation (MACS), or an enzymatic analysis. Examples of suitable endothelial progenitor cell markers for use in identifying the EPCs of the invention include CD34 (GENBANK Accession No. NP_001020280 or NP_001764) and fetal liver kinase 1 (Flk-1 or VEGFR-2; GENBANK Accession No. NP_002244). The expression of other endothelial progenitor cell markers, e.g., AC133 (GENBANK Accession No. 043490), CD31 (GENBANK Accession No. NP_000433), Tie-2 (GENBANK Accession No. Q02763), VE-cadherin (GENBANK Accession No. CAA56306), and eNOS (GENBANK Accession No. NP_000594), can also be assessed. See, e.g., Asahara, et al. (1997) *Science* 275: 964-7; Reyes, et al. (2002) *J. Clin. Invest.* 109: 337-46; Gehling, et al. (2000) *Blood* 95(10): 3106-12; Brugger, et al. (1994) *Blood* 84(5): 1421-6; Quirici, et al. (2001) *Brit. J. Haemat.* 115: 186-94; Vas, et al. (2001) *Circulation* 103: 2885-90; Shi, et al. (1998)

*Blood* 92(2): 362-; and Kawamoto, et al. (2001) *Circulation* 103: 634-7). These markers are highly, but not absolutely, specific. AC133 and CD34, markers of EPCs, are also present on the surface of hematopoietic stem cells, but not on any differentiated blood cells. The incidental capture of hematopoietic stem cells or other accessory cells along with the desired EPCs should not interfere in any way with the intended use of the instant EPCs. Indeed, it has been shown in dogs that the complete CD34$^+$ fraction, seeded onto graft surfaces ex vivo, does accelerate endothelialization after graft implantation (Bhattacharya, et al. (2000) *Blood* 95: 581-5).

Having demonstrated that $\alpha_4\beta_1$ and $\alpha_5\beta_1$ integrins, fibronectin, and vWF are essential in mediating EPC adhesion and migration, functions required for engraftment, re-endothelialization, and neovascularization in particular in acute lung injury, the EPCs of the present invention find application in promoting wound healing and angiogensis, ameliorating the symptoms of acute lung injury, and increasing the rate of survival of subjects with acute lung injury.

Thus, in one embodiment, the invention provides a method for promoting productive endothelial wound healing. The method involves administering to a subject in need of treatment a therapeutically effective amount of the isolated population of endothelial progenitor cells of the invention. Hereinafter, the term "wound" includes any injury to any portion of the body of a subject including, but not limited to, acute conditions such as thermal burns, chemical burns, radiation burns, burns caused by excess exposure to ultraviolet radiation such as sunburn; trauma-induced injuries including cuts, incisions, excoriations, those injuries sustained in automobile and other mechanical accidents, and those caused by bullets, knives and other weapons; ulcers such as pressure ulcer, plaster ulcer and decubitus ulcer; post-surgical injuries, as well as chronic conditions such as pressure sores, bedsores, conditions related to diabetes and poor circulation; a graft; dermatitis such as impetigo, intertrigo, folliculitis and eczema; and, as exemplified herein, a subject having or suspected of having ALI. Areas of the body which can be treated with the present invention include, but are not limited to, skin, muscle and internal organs. Efficacy of promoting wound healing with the present endothelial progenitor cells can be assessed by gross examination or histological inspection, wherein the administration of endothelial progenitor cells achieves the desired therapeutic result of providing, e.g., a 10%, 20%, 30%, 40%, 50% or more increase in the % closure of the wound as compared to a wound which has not been treated with endothelial progenitor cells. In accordance with this embodiment of the invention, EPCs can be administered alone or in combination with other agents known to promote wound healing. For example, agents such as IL-6 (Gallucci, et al. (2001) *J. Interferon Cytokine Res.* 21: 603-609; Sugawara, et al. (2001) *Cytokine* 15: 328-336; Erdag, et al. (2002) *Ann. Surg.* 235: 113-124; Nadeau, et al. (2002) *Microbes Infect.* 4: 1379-1387; Imanishi, et al. (2000) *Prog. Retin. Eye Res.* 19: 113-129; Gregory, et al. (1998) *J. Immunol.* 160: 6056-6061) and interferon-gamma have been shown to mediate proper wound healing, e.g., by modulating actin and collagen content, contractile capacity, and scar formation. See, e.g., Moulin, et al. (1998) *Exp. Cell Res.* 238: 283-293; Ahdieh, et al. (2001) *Am. J. Physiol. Cell Physiol.* 281: C2029-C2038; Cornelissen, et al. (2000) *J. Dent. Res.* 79: 1782-1788; Shtrichman, et al. (2001) *Curr. Opin. Microbiol.* 4: 251-259.

In addition to promoting wound healing, the instant endothelial progenitor cells were found to undergo morphogenic differentiation, a salient feature of neovascularization or angiogenesis, i.e., blood vessel generation. Accordingly, the present invention also provides a method for promoting angiogenesis using the endothelial progenitor cells of the invention. The method involves administering to a subject in need of treatment a therapeutically effective amount of the isolated population of endothelial progenitor cells of the invention. Subjects who could benefit from receiving the instant cells include those with a disease or disorder associated with a deficit of vessel development. Pathological states for which it may be desirable to increase angiogenesis include stroke, heart disease, infertility, ulcers, and scleredema. An increase in angiogenesis may also be desirable in transplantation or for artificial or in vitro growth of organs. The effect of treatment can be evaluated by many means known to those skilled in the art, e.g., microscopy for quantitative or qualitative measures of alterations in morphological features, e.g., tube or blood vessel formation or by an improvement in the symptoms of the disease or condition being treated, wherein the administration of endothelial progenitor cells achieves the desired therapeutic result of providing, e.g., a 10%, 20%, 30%, 40%, 50% or more increase in vessel formation compared to a subject not receiving treatment with the instant endothelial progenitor cells.

In addition to the assays disclosed herein, a number of animal-based assays for angiogenesis phenotypes are known to those of skill in the art and can be used to assay for efficacy of the instant EPCs in promoting angiogenesis. For example, a mouse corneal assay can be employed which involves implanting a growth factor-containing pellet, along with another pellet containing the endothelial progenitor cell, in the cornea of a mouse and observing the pattern of capillaries that are elaborated in the cornea.

The present invention also embraces a method for decreasing severity of lung injury and preventing pulmonary edema in acute lung injury by administering to a subject in need of treatment a therapeutically effective amount of the isolated population of endothelial progenitor cells of the invention. In another embodiment, the invention provides a method for increasing survival rate in acute lung injury by administering to a subject in need of treatment a therapeutically effective amount of the isolated population of endothelial progenitor cells of the invention.

Acute lung injury is damage to lung tissue caused by neutrophils which have infiltrated into the lungs. The neutrophils secrete mediators of lung injury, such as proteases and oxidants. These mediators lead to a massive loss in the selective permeability of both the capillary endothelium and alveolar epithelium. Examples of critical illnesses with acute lung injury are sepsis, SIRS and MODS. Successful application of the instant EPCs will result in a measurable decrease in pulmonary edema and decrease in severity of lung injury compared to a subject which does not receive treatment with EPCs. Such reduction in edema and lung injury affords increases in survival rates, e.g., as determined from a population of subjects receiving treatment with the EPCs as compared to a population not receiving treatment with EPCs. Efficacy of treatment can be evaluated by histology or pulmonary function, or number of patients surviving. Such end points are routinely practiced in the art. See, e.g., *Goodman & Gilman's The Pharmacological Basis of Therapeutics*, 11$^{th}$ *edition*. L. L. Brunton et al. (Eds.), McGraw Hill: New York.

In accordance with this invention, a therapeutically effective amount is the amount of EPCs that is sufficient to prevent, treat, reduce and/or ameliorate one or more symptoms of the disease or condition being treated. In some embodiments, a "therapeutically effective amount" is an amount which achieves an increase in the % closure of a wound or increase in the rate or amount of vascularization of a tissue. In another embodiment, a therapeutically effective amount is sufficient to reduce or eliminate a symptom of acute lung injury, e.g., pulmonary edema and microvessel permeability. In a further embodiment, a therapeutically effective amount is an amount sufficient to increase survival rate.

The EPCs of the invention can be administered in any suitable form, e.g., as a pharmaceutical composition, by combining the EPCs with a suitable pharmaceutical carriers as understood by practitioners in the art. Such carriers include saline, water, and the like. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000.

A therapeutically effective amount of EPCs can be administered in a single dose, or in several doses, for example daily, during a course of treatment. However, the effective amount of the EPCs can be dependent on the subject being treated, the severity of ALI and cause of ALI, and the manner of administration of the cells. "Administering" can be accomplished by introducing the therapeutically effective amount locally or systemically into the subject. The general term "administering a therapeutically effective amount to the subject" is understood to include all animals (e.g., humans, apes, dogs, cats, horses, and cows) that have or may develop a disease or condition disclosed herein. Systemic introduction can be accomplished by using an intravenous, intramuscular, transcutaneous or subcutaneous means. Such means could include introducing the therapeutically effective amount via injection, or via catheter. Desirably, the cells are administered in a manner that permits them to graft to the intended tissue site and reconstitute or regenerate the functionally deficient area. In this regard, topical application by use of creams, lotions, and the like are particular desirable for skin repair.

For example, in the treatment of ALI, EPCs are transplanted directly into the lung of the subject being treated. Transplants can be done using single cell suspension or small aggregates of from about $10^6$ to about $10^{18}$ progenitor cells (see, e.g., U.S. Pat. No. 5,980,887). The efficacy of EPC transplants can be assessed as disclosed herein in a mouse or sheep model of acute lung injury or using any other suitable model. For example, other models of sepsis-induced lung edema in mice include the cecal ligation-puncture (CLP) model (Baker, et al. (1983) Surgery 94: 331-335) and pneumonia induced by intra-tracheal (i.t.) Pseudomonas aeruginosa (Sadikot, et al. (2004) J. Immunol. 172: 1801-1808). Furthermore, U.S. Pat. No. 5,977,091 describes a pig model wherein LPS is delivered over one hour via a volumetric infusion pump.

EPCs of the invention also find application in screening for factors (such as solvents, small molecule drugs, peptides, peptidomimetics, polynucleotides, and the like) or environmental conditions (such as culture conditions or manipulation) that affect the characteristics of EPCs. In some applications, EPCs are used to screen factors that promote EPC engraftment (cell adhesion), e.g., via $\alpha_5\beta_1$ integrin-mediated cell adhesion; promote maturation; or promote proliferation and maintenance of such cells in long-term culture. For example, candidate maturation factors or growth factors are tested by addition to EPCs in different wells, and then determining any phenotypic change that results, according to desirable criteria for further culture and use of the cells.

Particular screening applications of this invention relate to the testing of pharmaceutical compounds in drug research. Such an application is generally discussed in the standard textbook In Vitro Methods in Pharmaceutical Research, Academic Press, 1997). Assessment of the activity of candidate pharmaceutical compounds generally involves combining the EPCs of this invention with the candidate compound, determining any change in adhesion, morphology, marker phenotype, or metabolic activity of the cells that is attributable to the compound (compared with untreated cells or cells treated with an inert compound), and then correlating the effect of the compound with the observed change.

The screening can be performed, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity. Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread.

In a particular application of the agents identified by such screening assays, it is contemplated that EPC engraftment can be increased by promoting $\alpha_5\beta_1$ integrin-mediated cell adhesion. Accordingly, a method for increasing EPC engraftment is also embraced by the present invention. This method involves contacting EPCs of the invention with an agent which promotes $\alpha_4\beta_1$ integrin-mediated cell adhesion thereby increasing EPC engraftment. Agents which can be used in accordance with such a method include peptides, peptidomimetics, adhesion promoting antibodies, or a pharmacological compound that enhances $\alpha_5\beta_1$ integrin mediated adhesion and signaling activity.

The invention is described in greater detail by the following non-limiting examples.

Example 1

Materials and Methods

Mice. C57BL/6J mice between 7 and 10 weeks of age were purchased from Charles River (Wilmington, Mass.) and housed in a pathogen-free Biological Research Laboratory vivarium facility. Experimental procedures involving the use of mice were approved by the Institutional Animal Care Committee.

EPC Culture Medium. Sterile phosphate-buffered saline (PBS), fetal bovine serum (FBS), antibiotics, and L-glutamine were purchased from INVITROGEN (Carlsbad, Calif.). EGM-2, which is a basal endothelial cell medium that contains 2% FBS and no growth factors cytokines or supplements, was from Cambrex (East Rutherford, N.J.). Human Vascular Endothelial Growth Factor-165 (hVEGF$^{165}$) was from R & D Systems (Minneapolis, Minn.). Human Vascular Endothelial Growth Factor-121 (hVEGF$^{121}$) was from Sigma (St. Louis, Mo.). Gelatin (0.2%) was prepared in PBS.

Complete EPC medium was prepared with the following reagents: Endothelial growth media-2 (500 ml), FBS (25 ml, final 5%), Hydrocortisone (0.2 ml), Basic fibroblast growth factor (bFGF) (2.0 ml), 2.5 ng/ml Heparin (1.0 ml), 50 ng/ml VEGF$^{165}$ (5.0 ml), 50 ng/ml VEGF$^{121}$ (5.0 ml), Human LONG™ R3 Insulin-like Growth Factor-I (IGF-I) (0.5 ml), Ascorbic acid (0.5 ml), GA-1000 (gentamycin and amphotericin-B) (0.5 ml), and 2.4 mM L-Glutamine (5.0 ml). Complete EPC media did not contain epidermal growth factor (EGF) so that EGFR expressing cells failed to proliferate.

Isolation and Purification of Bone Marrow (BM)-Derived Mononuclear Cells (MNCs). All procedures were under sterile conditions in a certified cell culture hood. Thirty C57BL/6J male and female mice (7-9 weeks old, 25-30 gm body weight) were sacrificed by $CO_2$ exposure and cervical dislocation. Tibia and femoras were removed using fine scissors. Adherent tissues were removed from the bones and the bones were placed in PBS. Both ends of the long bones were cut with the help of fine scissors so that the marrow could be flushed out. A 25-gauge needle (attached to a 2-ml syringe) was inserted at the proximal end of the femora or tibia and marrow was flushed into a 15-ml sterile tube using 1-2 ml of EGM2 medium containing 2% FBS. Bone marrow cells were washed once with complete PBS and resuspended in 15 ml of complete EPC media. Mononuclear cells were filtered through a 80 µm cell strainer to make a single cell suspension in complete EPC media.

A sterile 50 ml FALCON tube was filled with 20 ml of FICOLL-PAQUE under the hood. Fifteen ml of BM-derived MNC suspension was gently layered on the FICOLL-PAQUE without disturbing the FICOLL-PAQUE gradient. The cell suspension was centrifuged at 400×g (~1000 rpm) for 20 minutes at 4° C. The translucent buffy layer MNCs were gently removed using a sterile cotton-barrier tipped sterile pasture pipette. The BM-derived MNCs were resuspended in complete EPC media. The resuspended cells were centrifuged at 400×g (~1000 rpm) for 5 minutes at 4° C. The supernatant was discarded and the mononuclear cell pellet was resuspended in complete EPC media. The number of cells was counted using a hemocytometer.

Propagation and Expansion of MNCs as a source for EPCs. To specifically expand EPCs, cells were cultured onto dishes coated with 0.2% gelatin in complete EPC medium. MNCs ($5.0 \times 10^7$ cells) were plated onto each T75 cell culture flasks pre-coated with 0.2% gelatin. Complete EPC media (15 ml) was added to the flask. Flasks were incubated in a humidified $CO_2$ (5%) incubator for 6-7 days. To induce optimal cell adhesion, flasks were not handled or shaken. Media was removed at the end of 3 days to remove dead cells and fresh complete EPC media (10 ml) was added. At the end of 6-7 days, cells were examined under the microscope (100× magnification) to ensure the formation of adherent cell colonies. Typically 20-30 large and small colonies appeared in each T75 flask. This was considered passage-1. Media containing non-adherent cells (mostly monocytic cells) was removed and fresh complete EPC media was added. Fresh complete EPC media was added to the flask every $3^{rd}$ day. At day 14-15 (70% confluent), cells were detached using 0.25% trypsin-EDTA solution. Cells were expanded using complete EPC media. To expand further, cells were split at a 1:2 ratio.

At the end of 18-20 days, cells were analyzed by FACS flow sorting using anti-CD34$^+$ and anti-Flk-1 monoclonal antibodies. The percentage of CD34$^+$ and Flk-1$^+$ population was 85±2.5%, while anti-CD34$^+$ and anti-cKit$^+$ cells constituted 65±3.2%. EPCs used in the analysis disclosed herein were cultured between 1 to 4 passages, which was about 18-21 days in culture. This expansion protocol allowed for 2-5 population doublings. To maintain genomic stability, cells were not expanded or used beyond passage-5, which corresponds to about 28-30 days in culture.

Antibodies and Extracellular Matrix (ECM) Molecules. Hamster anti-rat/mouse $\alpha_1$ (Ha31/8) integrin, anti-Caveolin-1, anti-Grb2 monoclonal antibodies, and vitronectin (Vn) were purchased from BD Bioscience (Franklin Lakes, N.J.). Anti-rat-$\alpha_2$ (AF1740), anti-mouse VE-cadherin (AF1002) monoclonal antibodies, laminin-1 (Lm-1), and human plasma fibronectin (Fn) were purchased from R & D systems (Minneapolis, Minn.). Anti-mouse $\alpha_3$ integrin (Ralph 3.2) was obtained from Santa Cruz (Santa Cruz, Calif.). Anti-$\alpha_4$ (HP2/1) was purchased from ABCAM (Cambridge, Mass.). Anti-mouse $\alpha_5$ (5H1027/MFR4.B), anti-$\alpha_v$ (RMV7) and anti-Flk-1 (Avas 12A1) monoclonal antibodies were bought from Research Diagnostic (Concord, Mass.). Anti-rat/mouse $\alpha_6$ (GoH3) monoclonal antibody was purchased from Beckman Coulter (Fullerton, Calif.). Anti-Fak (2A7), anti-paxillin, and antiphosphotyrosine (4G10) mouse monoclonal antibodies, anti-phospho-Erk1/2, anti-phospho-Fak (Y397) and anti-$\alpha_v\beta_3$ (LM609) antibodies, and laminin-4 were purchased from Millipore (Temecula, Calif.). Type I Collagen solution was from Inamed Corporation (Irvine, Calif.). Cycloheximide, monensin, TRITC-phalloidin and anti-vinculin monoclonal antibody were purchased from Sigma-Aldrich (St. Louis, Mo.). Goat anti-rat fibronectin antibody was from Dr. Erkki Ruoslahti (La Jolla, Calif.). Rabbit anti-$\beta_1$ cyto and anti-$\beta_3$ cyto integrin polyclonal antibodies were from Dr. Guido Tarone (University of Torino, Torino, Italy). For blocking experiments, antibodies were dialyzed overnight in sterile 1× Tris-buffered saline, pH 7.5, at 4° C. to remove any traces of minor impurities including sodium azide. The integrity and concentration of antibodies were evaluated by SDS-PAGE.

Fluorescent Activated Cell Sorting (FACS). Because a limited number of cells at p1 and p2 were available, FACS analysis for integrin expression was not determined until passage 3. For FACS, the p3 EPCs were washed in PBS, pH 7.4, detached with 0.025% trypsin and 3 mM EDTA in PBS, pH 7.4, washed once in PBS containing $Ca^{2+}$ and $Mg^{2+}$, and passed through a cell strainer. The cells ($1 \times 10^6$) were then incubated with saturating amounts of control mouse IgG or anti-mouse (or rat) integrin monoclonal antibodies: anti-$\alpha_1$ (Ha31/8; Pharmingen), anti-$\alpha_2$ (AF1740), anti-$\alpha_3$ (Ralph 3.2), anti-$\alpha_4$ (R1-2), anti-$\alpha_5$ (5H1027/MFR4.B), anti-$\alpha_6$ (GoH3), and anti-$\alpha_v$ (RMV7) for 60 minutes at 4° C. In all cases, secondary labeling was performed for 1 hour with a donkey anti-goat (or rabbit) IgG conjugated to fluorescein isothiocyanate (FITC) or TEXAS RED (INVITROGEN, Carlsbad, Calif.). The cells were washed twice with PBS, fixed with 3.5% paraformaldehyde (PFA), and analyzed on a FACSCALIBUR flow cytometer (BD Biosciences).

Static Cell Adhesion Assays. Laminin-1 (Lm-1), Laminin-4 (Lm-4), Fibronectin (Fn), and Vitronectin (Vn) were prepared at concentrations of 12.5, 25, 50, 75, and 100 nM in Tris-buffered saline (20 mM Tris, pH 7.4 and 150 mM NaCl) according to established methods (Pozzi, et al. (1998) *J. Cell Biol.* 142: 587-94; Wary, et al. (1998) *Cell* 94: 625-34), and heat inactivated 0.2% bovine serum albumin (BSA) was included as control. Sterile microwells were coated overnight at 4° C. with increasing concentrations of the above substrates. EPCs were pre-treated with monensin for 20 minutes and with cycloheximide for 1 hour, cells were detached with 3 mM EDTA, pH 7.4, washed with PBS, and passed through a cell strainer to remove unwanted cell aggregates. The cells were collected and resuspended in EGM-2, 0.2% BSA, and 1× insulin/transferrin/selenium-A (ITS) supplemented with 1 mM $Mg^{2+}$ and $Ca^{2+}$. To a well, 100 µl of cell suspension ($0.5 \times 10^5$ cells/ml) was added and allowed to attach at 37° C. in a humidified $CO_2$ incubator for indicated times. Thereafter, unattached cells were removed by washing and fixed with 4% PFA containing 0.5% TRITON X-100. Fixed cells were washed, fixed in 20% methanol for 10 minutes, and stained with 0.5% crystal violet. Dyes were eluted in 100 µl of 100 mM sodium citrate, and absorbance was measured at 590 nm. Data were subjected to ANOVA to determine statistically significant differences in adhesion between the different ECMs. P<0.05 was considered statistically significant. For light microscopy images, cells were stained with eosin.

Immunofluorescence Microscopy. For focal adhesion staining, cells were seeded onto glass coverslips pre-coated with fibronectin (5.0 µg/ml), allowed to attach for 120 minutes, and fixed. Fixed cells were stained with anti-vinculin monoclonal antibodies and tetramethylrhodamine isothiocyanate (TRITC)-phalloidin for analysis by fluorescent microscopy. After incubating with an appropriate concentration of primary antibodies, glass cover slips were washed and mounted on slides with a drop of PROLONG ANTIFADE containing 4',6-diamidino-2-phenylindole (DAPI) (INVITROGEN). Fluorescence microscopy images were obtained with a ZEISS APOTOME microscope, and digital images were processed using AXIOVISION LE 4.5 (ZEISS) software and saved as TIFF images which were then converted to an EPS file using ADOBE PHOTOSHOP. Composite figures were prepared using QUARKEXPRESS 7.0 software, and QUARK files were converted to EPS images.

Cell Migration Assay. A modified Boyden chamber was used to measure haptotactic and chemotactic migration. ECM molecules, $VEGF^{165}$, and cell suspensions were prepared in EBM-2 containing 0.2% heat inactivated BSA. Briefly, a polycarbonate filter with 12-µm pores (CORNING COSTAR, Corning, N.Y.) was coated with ECM molecules (5 µg/ml), and experiments were performed using triplicate polycarbonate filters for each time point. Filters were placed on a 24-well chamber (CORNING COSTAR) containing 400 µl of $VEGF^{165}$ (50 ng/ml), mECs, and mEPCs (5,000 cells in 200 µl/well) were loaded into the upper compartment, and isotype matched IgG and anti-VEGF monoclonal antibodies (50 µg/ml) were added to the lower chamber. After incubation at 37° C. in 5% $CO_2$ for 6 hours, the filter was disassembled, the cells on the filter were fixed with 3.7% PFA, and stained with a 0.5% crystal violet. Non-migratory cells from the upper face of the filter were removed by Q-tip. The cells that migrated to the lower face of the membrane were counted using a light microscope at 200×. At least 6 random fields were chosen for each filter, and experiments were performed at least 3 times. Data were calculated as a percent cell migration. For example, out of ~5,000 cells plated onto the upper chamber of vitronectin+VEGF+IgG, only ~750 cells migrated to the lower face of the filter. This data was calculated as ~15% cell migration. Data represent the mean of three studies performed in triplicate.

Scratch Assay. To examine the ability of mEPCs to heal wounds, a scratch assay was performed. mEPCs were plated at high density ($10^7$ cells/ml) on glass coverslips, grown for 3 days in order to reach a confluent monolayer, and a white pipette tip (10 µl tip) was used to draw several scratch lines on to the monolayer. Cells that came off the glass coverslips were washed off with PBS, and remaining cells were provided with EBM-2 media supplemented with $VEGF^{165}$ (50 ng/ml). Cells were incubated at 37° C., and wound closure was monitored at 0, 4, and 8 hours.

Western Blot Analysis. To examine tyrosine phosphorylation of focal adhesion kinase (Fak) as a measure of productive cell adhesion event, cells were detached as described herein. Detached cells were kept in suspension for 45 minutes at room temperature. Thereafter, cells were replated onto dishes coated with indicated substrates at 37° C. in a $CO_2$ incubator. After 30 or 45 minutes, cells were solubilized in cell extraction buffer (50 mM HEPES, pH 7.5, 150 mM NaCl, 1% TRITON X-100, 25 mM sodium fluoride, 2 mM sodium orthovanadate, 1 mM sodium pyrophosphate, plus protease inhibitors), cell extracts were clarified by centrifugation, and protein concentrations determined by the BIO-RAD DC protein assay. Western analysis and detection protocols were performed according to established methods (Wary, et al. (1996) Cell 87: 733-43; Pozzi, et al. (1998) supra; Wary, et al. (1998) supra).

Morphogenic differentiation of mEPCs. bFGF- and VEGF-induced morphogenic differentiation of mEPCs on type I collagen matrix was performed according to known methods with minor modifications (Humtsoe, et al. (2003) EMBO J. 22: 1539-54; Wary, et al. (2003) Mol. Cancer 2: 25). Briefly, mEPCs were detached from dishes with 3 mM EDTA, washed with PBS, suspended in defined medium (EBM-2 medium containing 5% FBS, 1× insulin, transferrin, and selenium (ITS)), and seeded onto collagen matrix. Approximately $0.1 \times 10^6$ mEPCs were incubated with 50 µg/ml of control IgG, anti-$\alpha_1$, anti-$\alpha_2$, anti-$\alpha_3$, anti-$\alpha_4$, anti-$\alpha_5$, anti-$\alpha_6$, and anti-$\alpha_v\beta_3$ integrin monoclonal antibodies on ice for 45 minutes. The mEPCs were then washed and resuspended in defined medium, and cultured with FGF-2 (20 ng/ml) and VEGF (50 ng/ml) for 16 hours in a humidified $CO_2$ incubator at 37° C. Cells were fixed with 4% PFA, and after washing with PBS, photographs were taken under a phase-contrast microscope. For quantification of branching points, at least 10 random fields were chosen. Experiments were repeated three times.

Quantification of Pulmonary Microvascular Permeability and Edema Formation. The Pulmonary filtration coefficient ($K_{f,c}$) was measured to determine pulmonary microvascular permeability to liquid (Vogel, et al. (2000) Physiol. Genomics 4: 137-145). Briefly, after a standard 30-minute equilibration perfusion, the outflow pressure in the isolated-perfused mouse lung preparation was rapidly elevated by 10 cm $H_2O$ for 5 minutes, and then returned to normal. The lung wet weight changes were in a ramp-like fashion, reflecting net fluid transvascular fluid filtration. At the end of each experiment lungs were dissected free of non-pulmonary tissue, and blood-free lung dry weight was determined. $K_{f,c}$ (ml/min/cm$H_2$0/dry g) was calculated from the slope of the recorded weight change, normalized to the pressure change and to the lung dry weight.

To assess the leakiness of pulmonary microvessels, the rate of pulmonary edema formation was monitored continuously based on lung wet weight change. Weight changes of lungs obtained from different groups were followed until maximal edema or for 90 minutes after the start of the experiment.

Example 2

Purification and Expansion of Mouse EPCs

Under an appropriate physical and chemical microenvironment, stem cells generate a diverse range of multipotent progenitor cells. These multipotent progenitor cells in turn give rise to several different limited potential progenitor cells, which produce one or more specialized differentiated cell types.

Stem cells are highly abundant and active during embryonic development, but their pool diminishes in adult life. For example, neural and endothelial progenitor cells (EPCs) are found at diminished levels in adult. However, some adult organs such as skin, intestinal epithelium, liver, and bone marrow have higher levels of self renewing stem cells. Bone marrow serves as one of the main sources for hematopoietic stem cells, as well as non-hematopoietic stem cells, from which several different progenitor cells can be isolated and expanded ex vivo.

Cell surface markers of EPCs include CD34, AC133, and Flk-1. EPCs may also express mature endothelial cell markers including CD31, Tie-2, VE-cadherin, and eNOS antigens. However, these same markers are also found in hematopoietic stem cells. In addition to these markers, EPCs may also express $\beta_2$ family of leukocyte integrins (Chavakis, et al. (2005) *J. Exp. Med.* 201: 63-72).

Two different subsets of EPCs have been identified, early-out-growth and late-out-growth EPCs. The early out-growth EPCs are presumably non-proliferative, whereas late out-growth are proliferative (Hur, et al. (2004) *Arterioscler. Thromb. Vasc. Biol.* 24: 288-293). The method of this invention provides a population of cells as a source for both early- and late-out-growth EPCs. The method employs an Endothelial Growth Media (EGM)-2 formulation, which does not include epidermal growth factor (EGF), as this cytokine favors differentiation of epithelial cells. In addition to VEGF$^{165}$, the method also employs VEGF$^{121}$ which facilitate the differentiation and maintenance of endothelial cells. The addition of these two VEGF isoforms was observed to enhance ex vivo propagation and expansion of adherent EPCs, which also synthesize $\alpha_5\beta_1$ integrin, express von Willebrand Factor (vWF), and deposit fibronectin proteins.

Using this protocol an adherent sub-population of cells (hereafter referred to as passage 1 (p1) mEPCs) appeared as early as 6-7 days. P1 cells were expanded up to p5 and their morphology was examined using light microscopy. Cells termed p2 and p3 cells (equivalent to 2 population doublings) were early-growth mEPCs (15-17 days in culture). These cells were 60-70% adherent and had cobblestone, endothelial cell-like morphology. However, by p4 (19-20 days in culture), mEPCs became more homogeneous morphology, and mEPCs that were cultured up to p5 (21-22 days in culture) displayed an elongated structure. To minimize cell culture induced artifacts, all experiments were performed using p3 and p4 mEPCs. Western blot analysis was subsequently performed to determine the expression of known endothelial cell antigens. The results of this analysis indicated that the expression of Flk-1 (also known as VEGFR-2) in mouse lung endothelial cells (mEC$_3$, passage 3) was minimal. Interestingly, p1 to p3 mEPCs showed a steady increase in Flk-1 expression, while the expression of Flk-1 was robust at p4 and p5. A similar pattern of expression was observed for $\beta_1$ and $\beta_3$ integrins and caveolin-1. In contrast, no change in expression was detected for adapter protein Grb2. Increased expression of $\beta_1$ and $\beta_3$ integrin subunits coincided with adherent phenotypic appearance, and formation of elaborate actin stress fiber and focal adhesion sites. These data indicate that ex vivo expansion of BM-derived mononuclear cells acquire an adherent phenotype as they begin expressing $\beta_1$ and $\beta_3$ integrin subunits.

EPCs were also immunostained with monoclonal antibodies to c-kit, CD34 and CD31 and examined by fluorescence microscopy and FACS analysis. After 14 days in culture, the cells exhibited an increase in the expression of c-kit, CD34 and CD31, conventional markers for EPCs.

Example 3

BM-Derived mEPCs Express a Subset of $\beta_1$ Integrins

Several observations indicated that ex vivo-expanded mEPCs were adherent and anchorage-dependent cells. Since integrins control cell adhesion and anchorage-dependent phenotypes, the expression levels of various integrin polypeptides on the surface mEPCs was also determined. For integrin expression analysis, p3 mECs and mEPCs (15-16 days) were used in combination with specific anti-mouse (or rat) antibodies and FACS. This analysis indicated that mECs and mEPCs expressed the laminin/collagen-binding $\alpha_1$ and $\alpha_2$ integrins (which heterodimerize with $\beta_1$ subunits to form $\alpha_1\beta_1$ and $\alpha_2\beta_1$ integrins) at comparable levels. The expression of $\alpha_3$ integrin, which combines with the $\beta_1$ subunit to form the $\alpha_3\beta_1$ integrin heterodimer that interacts with laminin-4, was also consistently observed. mECs expressed insignificant level of $\alpha_4$ integrin. In contrast, mEPCs expressed higher level of integrin $\alpha_4$. Both mECS and mEPCs expressed equivalent levels of integrin $\alpha_5$ subunit. Integrin $\alpha_4$ and $\alpha_5$ subunits combine with $\beta_1$ subunit to form $\alpha_4\beta_1$ and $\alpha_5\beta_1$ integrins, known receptors for fibronectin. The $\alpha_v$ subunit was also detected. This subunit interacts with $\beta_1$ and $\beta_3$ integrin subunits. Compared to $\alpha_4$ and $\alpha_5$ subunits, the expression of the $\alpha_6$ subunit was weak. Integrin $\alpha_6$ can combine with $\beta_1$ and $\beta_4$ subunits to form $\alpha_6\beta_1$ and $\alpha_6\beta_4$ integrins, respectively; however, the expression of the integrin $\beta_4$; subunit was not detected. VE-cadherin and Flk-1 antigens were included as controls. These data show that EPCs predominantly express a subset of $\beta_1$ integrins. In so far as $\alpha_4\beta_1$ integrin has been shown to provide velocity to cell migration, whereas $\alpha_5\beta_1$ integrin mediates stable adhesion (engraftment) EPCs of the invention are likely to be homing- and adhesion-competent.

Example 4

Adhesion of mEPCs onto Purified ECM Proteins

A cell adhesion assay was performed to examine the ability of mEPC integrins to bind specific extracellular matrix (ECM) molecules by preparing increasing concentrations of fibronectin (Fn), vitronectin (Vn), laminin-1 (Lm-1), and laminin-4 (Lm-4). Pilot experiments were performed to determine the optimal concentration of ECM components required for mEPC adhesion. Heat-inactivated BSA was included as a negative control and used to block ECM pre-coated dishes. Binding of mEPCs to heat-inactivated BSA was minimal and considered baseline. Concentration-dependent adhesion of mEPCs to Lm-1, Lm-4, Fn, and Vn was observed at lower concentrations (12.5, 25, and 50 nM). In contrast, higher concentrations of ECM (75 and 100 nM) did not promote a further increase in mEPC adhesion. Addition of EDTA (1 and 2 mM) blocked integrin-mediated cell adhesion, indicating that mEPC attachment required the presence of $Ca^{2+}$ and $Mg^{2+}$. Interestingly, mEPCs plated on Fn and Vn were spread compared to those plated on Lm-1 or Lm-4.

Example 5

Cell Junction Formation

It was subsequently determined whether EPCs could promote cadherin mediated cell-cell junctions. To determine whether EPCs could promote assembly of cadherin-mediated adherens junctions (AJs), confluent human pulmonary arterial endothelial cells (HPAECs) were grown on gold electrodes and challenged with thrombin, an agent known to disrupt AJs. Junction permeability was then determined by TER. To determine the effect of EPCs on AJ formation, HPAECs were co-cultured with EPCs (ratio 1:1) and challenged with thrombin (4 U/ml). HPAECs with thrombin exhibited a 55% decline in TER relative to control cells without thrombin. In contrast, EPCs co-cultured with HPAECs consistently showed an absence of decrease in TER in response to thrombin. In separate controls, co-culture of mouse endothelial cells with HPAECs did not prevent the thrombin-induced decrease in TER. Thus, EPCs maintained endothelial junction integrity. This finding was supported by immunohistochemical and western blot analysis which showed reduced junction disassembly when EPCs were co-cultured with endothelial cells.

Moreover, it was observed that, over time, EPC interaction with endothelia led to increased expression of VE-cadherin. HPAECs were incubated with rhodamine-labeled EPCs for 3 days and challenged with 10 nM thrombin at 37° C. After fixation, HPAECs, and EPCs co-cultured with HPAECs were incubated with anti-VE-cadherin antibody overnight at 4° C. Cells were visualized after incubation with ALEXA 488 goat anti-mouse antibody. Cells were stained with DAPI to visualize nuclei. VE-cadherin in HPAECs was assessed at time 0 and after thrombin treatment (at 10 minutes, 30 minutes, and 60 minutes). Thrombin induced junctional disruption by 10 minutes with more pronounced disruption apparent by 30 minutes and 1 hour. Beginning as early as 10 minutes, VE-cadherin exhibited a discontinuous pattern of staining in the plasma membrane. However, with EPC addition, VE-cadherin remained plasma membrane-associated and AJs appeared intact, indicating that EPCs prevented disruption of endothelial junctions. Furthermore, upon incubation of confluent HPAECs with EPCs and challenge with LPS (10 μg/ml for up to 18 hours), it was observed that VE-cadherin expression increased. These data indicate that EPCs facilitate the re-annealing of the junctional barrier by preventing VE-cadherin disassembly and induce VE-cadherin expression.

It was next determined whether adhesion of mEPCs to fibronectin induced the formation of focal adhesion sites (ECM cell junctions), tyrosine phosphorylation of Fak, and Erk1/2 activation. It was observed that adhesion of mouse lung endothelial cells (mEC) (positive control) and mEPCs onto fibronectin induced formation of focal adhesion sites. Focal adhesion site formation was associated with a highly organized cytoskeleton with actin containing microfilaments and fiber-like structures. Thus, mEPC integrins are adhesion-competent and $\alpha_4\beta_1$ and $\alpha_5\beta_1$ integrins are functional on fibronectin and induce formation of focal adhesion sites.

The finding that adhesion of mEPCs formed focal adhesion sites on fibronectin pointed to the involvement of intracellular signaling. Thus, it was determined whether adhesion of mEPCs to fibronectin leads to changes in tyrosine phosphorylation of Fak. This analysis showed tyrosine phosphorylation of Fak in mEPCs in response to adhesion onto Lm-1, Lm-4, Fn, and Vn, whereas BSA failed to do so. In addition, Erk1/2 phosphorylation was observed. Thus, mEPC integrins aggregate to form cell-ECM adhesion junctions and induce tyrosine phosphorylation of Fak.

Example 6

Migration of Cells in Response to ECM and VEGF

To study the haptotactic and chemotactic behavior of mECs and mEPCs in response to ECM and VEGF stimulation, an in vitro migration assay was performed using the modified Boyden chamber. In this assay, cells from the upper compartment migrate through an ECM-coated porous membrane to a lower face. The lower chamber remains partially submerged in EBM-2 media supplemented with VEGF (50 ng/ml) that is provided as a chemoattractant. To determine the chemotactic response specifically due to VEGF, isotype-matched IgG and anti-VEGF monoclonal antibody were added to the lower chamber. In pilot experiments, it was found that mECs and mEPCs migrated in response to VEGF, but not to PDGF stimulation. Thus, VEGF was selected for further studies. VEGF in the presence of control IgG stimulated migration of both mECs and mEPCs. Among the ECM components used, Vn showed the highest haptotactic and chemotactic activity toward mECs and mEPCs in presence of VEGF. The migratory response was inhibited by the addition of anti-VEGF monoclonal antibody regardless of the ECM component used. Migration through BSA-coated pores was considered baseline.

To examine the role mEPC in wound healing, a scratch assay was subsequently performed. This experiment was carried out in the absence or presence of VEGF, and showed that mEPCs migrated and closed wounds over a period of 8 hours. These data indicate that mEPCs respond to ECM and VEGF stimulation.

Example 7

Inhibition of mEPC Morphogenic Differentiation

During the active sprouting phase of neovascularization, adherent endothelial cells proliferate and reorganize in a collagen-rich matrix and angiogenic mediators such as bFGF and VEGF activate endothelial cells plated on type I collagen matrix. Therefore, a type I collagen matrix protein was used to recapitulate the in vivo microenvironment of endothelial cells at the sprouting ends of blood vessels. Upon activation, endothelial cells become elongated, migratory, and form mosaics of cell-cell and cell-matrix adhesion structures, a process termed morphogenic differentiation which is considered an in vitro correlate of neovascularization (Wary (2004) supra). To determine whether mEPCs undergo a similar morphogenic differentiation, mEPCs were cultured using a type I collagen matrix as described (Humtsoe, et al. (2003) *EMBO J.* 22: 1539-54; Wary, et al. (2003) *Mol. Cancer* 2: 25). To assess if morphogenic differentiation was mediated by integrins, mEPCs were incubated with indicated monoclonal antibodies. This analysis showed that morphogenic differentiation of mEPCs was not affected by addition of anti-rat IgG, anti-rat $\alpha_1$, $\alpha_2$, $\alpha_3$, $\alpha_6$, or $\alpha_v\beta_3$ antibodies. In contrast, anti-rat $\alpha_4$ and $\alpha_5$ blocked all aspects of morphogenic differentiation of mEPCs. Together, these observations indicate that $\alpha_4\beta_1$ and $\alpha_5\beta_1$ integrins play a key role in the ability of mEPCs to undergo morphogenic differentiation.

Example 8

Activation of RhoA and Rac1 in Endothelial Cells

Monomeric RhoGTPases, RhoA, Rac1 and Cdc42, may be crucial for the incorporation of EPCs into the pulmonary microvessel wall, and thus contribute to the formation of endothelial barrier. Thus, experiments were carried out to determine the activation of these RhoGTPases in endothelial cells incubated with EPCs. HPAECs were grown to confluence on gelatin-coated T75 flasks for 3 days and subsequently incubated with EPCs for 5 minutes, 30 minutes, 2 hours, 4 hours or 18 hours. Active, endothelial membrane-associated GTP-bound RhoA, Rac1 and Cdc42 activities were determined using conventional methods (Kouklis, et al. (2004) *Circ. Res.* 94: 159-166) after removal of EPCs by washing. Proteins in an identical gel were transferred to nitrocellulose membrane and immunoblotted with either anti-RhoA, anti-Rac1, or anti-Cdc42 antibody. Immunoblotting of HPAECs showed that activated RhoA protein increased maximally by 30 minutes after EPC addition. However, activated Rac1 protein was increased in 2 hours after EPC addition and remained elevated thereafter. On the other hand, Cdc42 was not activated. These findings indicate that endothelial cell retraction, induced by RhoA activation-mediated endothelial contraction, may be a crucial step in mediating EPC engraftment. In contrast, activation of Rac1 in endothelial cells, known to be an inducer of EC spreading, may promote integration of EPCs into the monolayer, thereby sealing the endothelial barrier.

Example 9

Transcription Factor FoxM1 in EC Regeneration

To gain insights into the function of FoxM1 in endothelial repair following vascular injury, FoxM1 was in activated in the mouse endothelium using the Tie-2 promoter/enhancer-driven Cre (Kisanuki, et al. (2001) *Dev. Biol.* 230: 230-242). Lung microvascular endothelial barrier function was assessed by measuring pulmonary microvascular filtration coefficient ($K_{f,c}$) and edema formation after i.p. injection of LPS (5 mg/kg body weight). $K_{f,c}$ values at 6 hours after LPS treatment was not significantly different between FoxM1 conditional knock out (CKO) mutant and wild-type lungs. In wild type lungs, $K_{f,c}$ returned to baseline in 48 hours; however, $K_{f,c}$ in FoxM1 CKO lungs remained significantly elevated at 48 and 96 hours after LPS treatment.

Lung wet weight changes were also measured after LPS challenge. As evident from the precipitous rise in lung weight, edema formation was prominent in FoxM1 CKO lungs beginning at 48 hours after LPS treatment and continued through 96 hours, but was not seen in wild-type lungs. Thus, LPS induced similar vascular injury in FoxM1 CKO and wild-type lungs as evidenced by the comparable $K_{f,c}$ values at 6 hours. The crucial difference seen in FoxM1 CKO lungs was the persistent microvascular injury resulting in the protracted increase in vascular permeability.

Strikingly, a higher dose of LPS (12 mg/kg body weight) resulted in a significantly greater mortality rate of FoxM1 CKO mice than wild-type mice; 70% of FoxM1 CKO died within 96 hours of LPS challenge whereas only 10% of wild-type mice died in this same period. Fluminant pulmonary edema was the cause of death in FoxM1 CKO mice.

To determine whether FoxM1 can be activated after the onset of vascular injury, mice were challenged by i.p. injection of LPS. Quantitative real-time RT-PCR (QRT-PCR) showed 4-fold increase of FoxM1 mRNA expression in wild-type lungs at 3 days post-LPS challenge. Recruitment of inflammatory cells into the lungs and vascular leakage occurred as early as 3 hours after LPS challenge with maximal lung microvessel injury at ~24 hours. Thus, the time course of FoxM1 expression paralleled only the recovery phase of LPS-induced injury. A higher dose of LPS (7.5 mg/kg body weight) resulted in a 10-fold increase in FoxM1 mRNA expression in wild-type lungs at day 3, indicating that the level of expression is coupled to severity of injury. In addition, two other inflammatory mediators, TNFα and $H_2O_2$, significantly induced FoxM1 mRNA expression in primary endothelial cultures isolated from wild-type mouse lungs.

It was subsequently determined whether the defective vascular repair seen in FoxM1 CKO mice following LPS-induced injury was attributed to decreased endothelial cell proliferation. Mice were treated with LPS, and cell proliferation was measured by BrdU incorporation. Cryosections of lungs (3 to 5 μm thick), collected 72 hours after LPS challenge, were stained with FITC-conjugated anti-BrdU antibody to identify proliferating cells, whereas nuclei were counterstained with DAPI. From 3 to 4 consecutive cryosections from each mouse lung were examined, and the average number of BrdU positive nuclei per 2,000 nuclei was used as the value for the mouse. This analysis indicated that wild-type lungs exhibited increased cell proliferation that peaked at 72 hours, a response that paralleled the time course of FoxM1 mRNA induction. Cell proliferation in FoxM1 CKO and wild-type lungs was comparable at 24 hours following LPS challenge; however, proliferation was markedly impaired in FoxM1 CKO lungs at 48 and 72 hours.

The reduced cell proliferation seen in FoxM1 CKO lungs indicated that FoxM1 plays a crucial role in endothelial cells proliferation and barrier repair. This was addressed using endothelial cells isolated from either FoxM1 CKO or wild-type mouse lungs. Proliferation of endothelial cells cultured from FoxM1 CKO lungs was markedly reduced compared with those from wild-type lungs. After 5-7 days in culture, the FoxM1 CKO endothelial cells were less than 20% confluent, whereas wild-type endothelial cells were >80% confluent. However, primary cultures of non-endothelial cells from FoxM1 CKO lungs, which retained the FoxM1 fl/fl targeted allele, displayed similar growth rates compared with non-endothelial cells from wild-type lungs.

To examine mechanisms of proliferative defects seen in FoxM1 CKO endothelial cells, small-interfering RNA (siRNA) were transfected in human microvascular endothelial cells to suppress FoxM1 expression. FACS analysis showed significant accumulation of 4N DNA content in human microvascular endothelial cultures treated with FoxM1 siRNA, indicating defective progression from G2 into mitosis. FoxM1-depleted human microvascular endothelial cells also exhibited a polyploid (8N) peak, indicating endoreduplication caused by entry into a second round of DNA replication without completion of mitosis. As seen in FoxM1 CKO lungs, expression of the cell cycle inhibitor $p27^{KiP1}$ was significantly upregulated and nuclear staining of $p27^{KiP1}$ was prominent in FoxM1-deficient endothelial cells. Both Cdk1 and Cdk2 activities were markedly decreased in FoxM1-deficient endothelial cells and a set of genes essential for cell cycle progression including several cyclins, Cdc2 and Cdc25C, were significantly decreased. Taken together, these results demonstrate that FoxM1 is required for EC proliferation and therefore may be crucial for the recovery of endothelial barrier function induced by EPC transplantation.

Example 10

EPCs Deposit Fibronectin-Rich Matrix

It is known that ECs express fibronectin and increased levels of fibronectin are found in blood vessel walls concurrent with endothelial cell proliferation and capillary growth (Clark, et al. (1982) *J. Invest. Derrnatol.* 79: 269-276; Clark, et al. (1982) *J. Exp. Med.* 156: 646-651). Thus it was determined whether EPCs produce their own fibronectin matrix. Mouse lung endothelial cells (mECs, control cells) and mEPCs were cultured on gelatin-coated glass coverslips for 72 hours. Cells were cultured in complete media composed of 5% FBS with EGM-2 EC supplement added. Cells were fixed, incubated with control IgG or anti-rat fibronectin monoclonal antibody, and incubated with rabbit anti-goat IgG conjugated to fluorescein isothiocyanate (FITC). Moderate synthesis and deposition of fibronectin matrix by mECs was observed. Strikingly, mEPCs synthesized and deposited much greater amounts of fibronectin. It was also observed that the fibronectin-deposited by both mECs and mEPCs assembled into the ECM. To address whether cell passage number influenced fibronectin production, total cell lysates were prepared from EPCs that were expanded to passages 1-5 and subsequently subjected to western blot analysis at each passage. These data were compared with those of lysates from mECs (control). EPCs expressed >20-fold fibronectin expression compared to mECs at the same passage. In addition, it was observed that EPCs expressed high levels of immature von Willebrand Factor (vWF). Thus, EPCs expressed functional fibronectin receptor integrins $\alpha_4\beta_1$ and $\alpha_5\beta_1$ and synthesized, deposited, and assembled fibronectin in the ECM. These data indicated that EPCs may be engraftment-competent cells in the intact lung microcirculation.

Example 11

Retention of EPCs In Vivo

The fate of introduced EPCs in lung microvessels was analyzed. Cultures of bone marrow-derived EPCs were labeled with rhodamine-based red fluorophore CMTMR and $5 \times 10^5$ cells were delivered to the pulmonary vascular bed of wild-type mice via external jugular vein injection. Mice were sacrificed at 20 minutes and 24 hours after injection, and lung sections were examined by fluorescence microscopy. At 20 minutes, EPCs were seen within pulmonary microvessels, and at 24 hours EPCs were also found in pulmonary microvessels lining the alveolar-capillary septum. Thus, EPCs were retained in the pulmonary microvessels at the level of the alveolar-capillary septum for at least the 24 hour study period.

Example 12

Barrier Function of EPCs

It was subsequently determined whether EPCs had an effect on junctional endothelial barrier function. This was determined by measuring, in real-time, transendothelial electrical resistance (TER) of human pulmonary arterial endothelial cells (HPAECs) in a confluent monolayer. HPAECs were initially seeded onto gold microelectrodes and cultured to confluency. Growth medium containing 10% FBS was replaced with 0.1% FBS EGM2-MV medium. Addition of EPCs to HPAECs in increasing numbers (0, 500, 1000 or 5000 cells/per well) increased TER, whereas addition of endothelial cells to an endothelial cell monolayer had no effect on TER. These data indicate that EPCs have an effect in strengthening endothelial junction barrier likely mediated by physical interaction and release of paracrine mediators.

Figure 1:
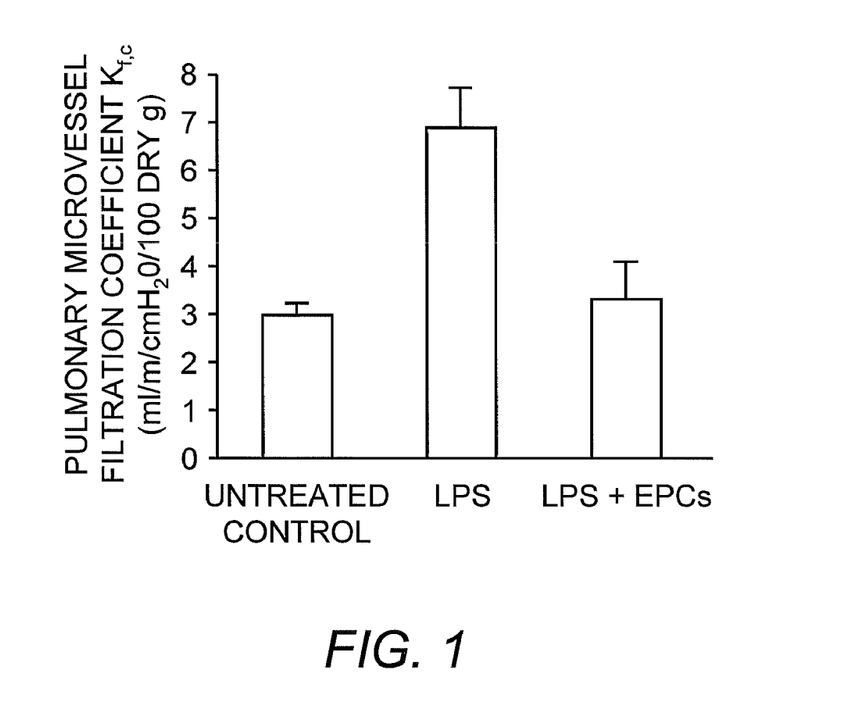
FIG. 1 shows the protective effect of EPCs which prevent LPS-induced lung microvascular barrier leakage. N=15-20 per group. Bars represent SEM.

To demonstrate an in vivo effect, lung vascular permeability were determined in LPS challenged mice receiving EPC transplantation. Mice challenged with LPS served as control. Both groups were challenged with 7.5 mg/kg LPS i.p. for 6 hours. Pulmonary microvascular filtration coefficient ($K_{f,c}$), a measure of lung microvessel permeability, was determined. As shown in FIG. 1, EPCs provided a protected effect by preventing LPS-induced lung microvascular barrier leakage.

Example 13

Treatment with EPCs Reduces ALI Mortality

Bone marrow EPCs and lung microvessel ECs (mECs, which were used as cells for comparison) were isolated from C57/BL6 syngeneic male mice, 6-8 weeks of age. Upon isolation, bone marrow cells were purified and expanded to passage 3 as described herein. Recipient mice were exposed to whole body sub-lethal γ-irradiation (5Gy) to suppress activity of endogenous bone marrow cells and allowed to recover for 72 hours prior to challenge with LPS (i.p. 7.5 mg/kg body weight). Either mEPCs or mECs were administered i.v. after a 6 hour LPS treatment, a time when the lung vascular permeability increase was maximal. Each mouse received 350,000 cells in 150 µl of PBS i.v.

Figure 2A:
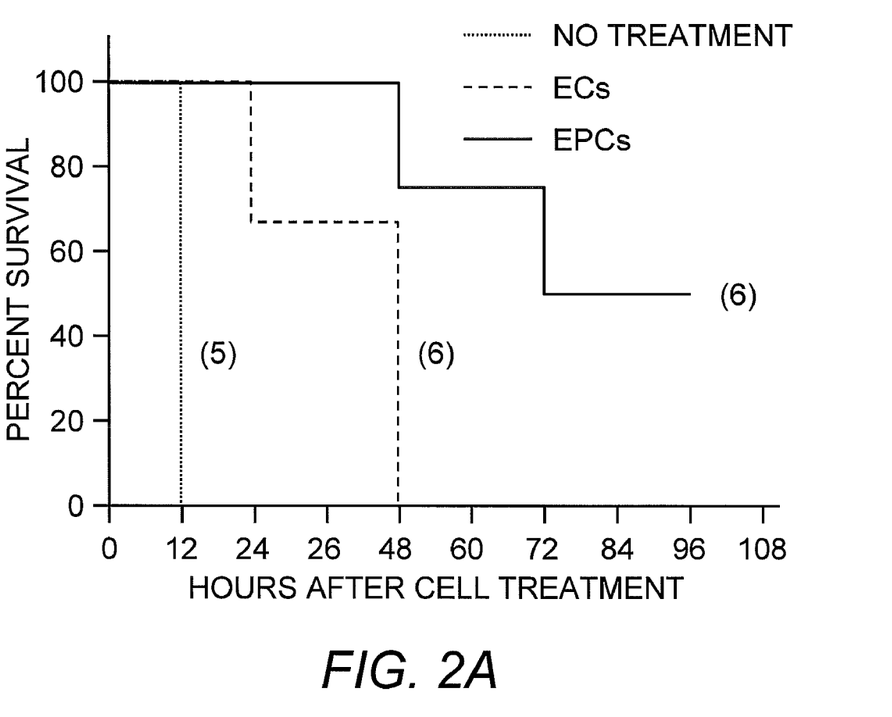
FIG. 2A, mEPC treatment increases survival. Cells were injected 6 hours post LPS challenge (i.p., 7.5 mg/kg body weight). Mouse EPC injection provided 50% survival, whereas mECs failed to protect. n=15.

Administration of mEPCs resulted in significantly greater survival following LPS challenge than mice injected with mECs (FIG. 2A). These results show that administration of selected mEPCs after the LPS challenge reduced mortality to a greater extent than mECs. Also, the protection cannot be ascribed to release of endogenous EPCs, indicating the therapeutic potential of exogenously administered EPCs.

Example 14

EPC $\alpha_5$ Integrin and Fibronectin Expression Contribute to the EPC-Mediated Reduction in Mortality and Lung Edema Formation induced by LPS The contribution of EPC $\alpha_5$ integrin and fibronectin receptor-ligand pair in mediating the reduction in mortality after treatment with EPCs was subsequently determined. Studies were made using mEPCs transduced with shRNA constructs to silence $\alpha_5$ integrin and fibronectin genes. Control mice received mEPCs transduced with $\alpha_v$ integrin shRNA. Three to four different shRNA retroviral constructs were tested for each target gene. Infection was carried out for 16 hours and constructs shown to down-regulate expression by >70% were selected for further studies. In mouse studies, mEPCs transduced with retroviral shRNA constructs were administered after LPS challenge as described herein.

Figure 2B:
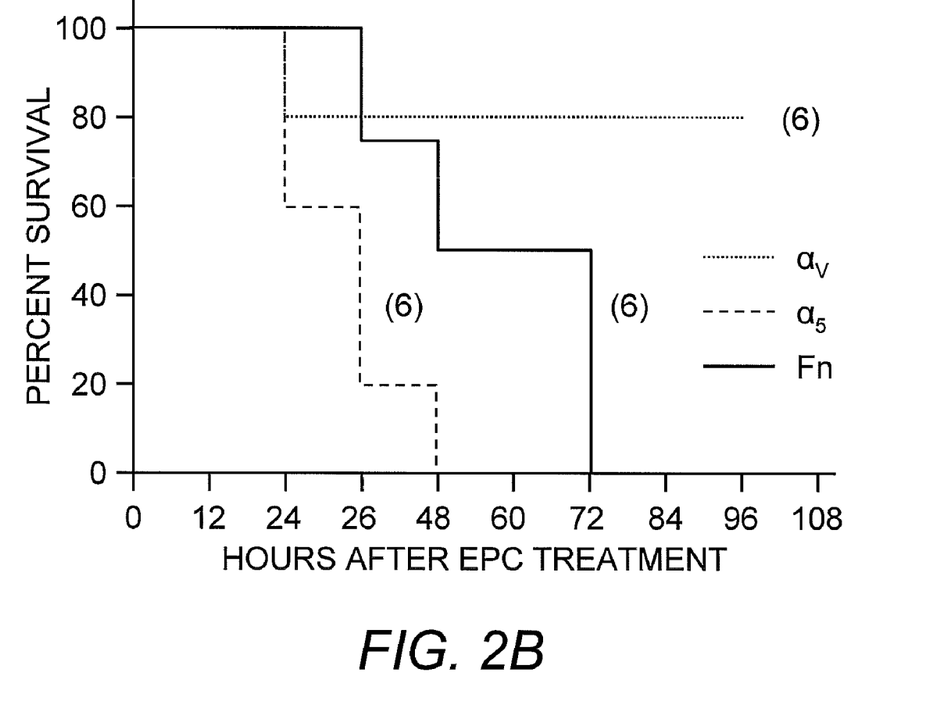
FIG. 2B, Silencing of $\alpha_5$ integrin and fibronectin in mEPC failed to protect, whereas silencing of $\alpha_v$ integrin (control) had no significant effect. N=15.
Figure 2C:
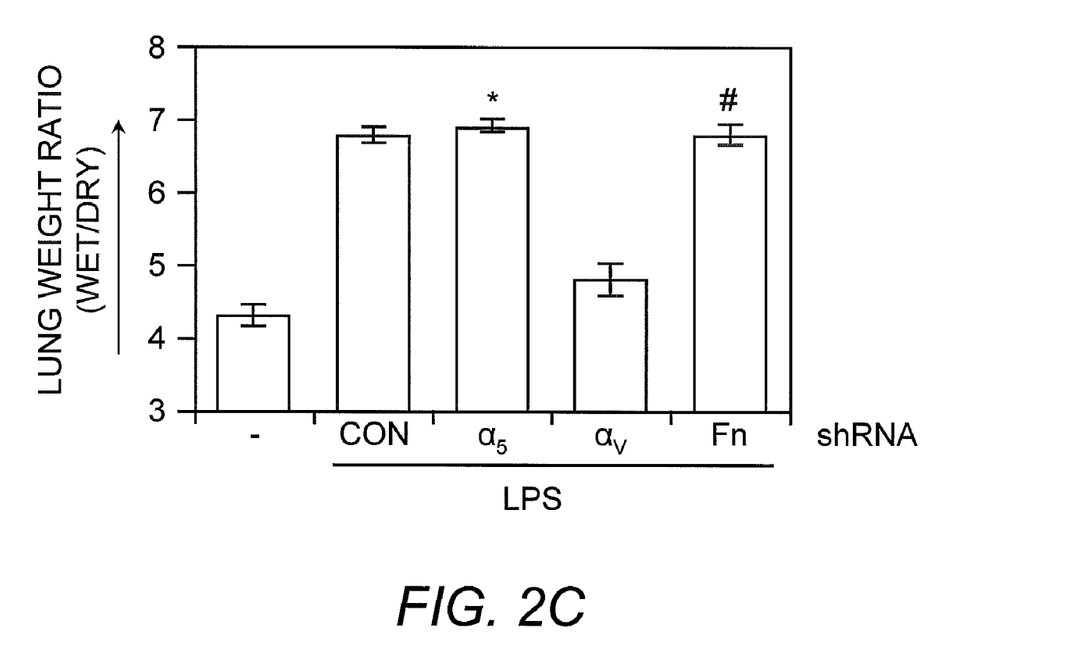
FIG. 2C, Lung edema formation in mEPC-treated mice following LPS challenge (i.p., 7.5 mg/kg body weight). Lungs were obtained at 36-72 hours after cell treatment. Con, Control (LPS alone); Fn, fibronectin. Data are expressed as mean±SEM. n=5-6, *p<0.05 vs. no LPS treatment (−); #p<0.01 vs. no LPS treatment (−).

This analysis indicated that silencing of fibronectin (a $\alpha_5\beta_1$ integrin ligand) and $\alpha_5$ integrin abolished the ability of mEPCs to protect mice challenged with LPS, whereas silencing of $\alpha_v$ integrin had a protective effect (FIG. 2B). Significant pulmonary edema was observed after LPS challenge as the result of suppression of fibronectin and $\alpha_5$ integrin in EPCs (FIG. 2C). These studies indicate that lung vascular retention of EPCs mediated by fibronectin and $\alpha_5$ integrin may be crucial for vascular endothelial barrier protection and thus reduce lung edema formation. The restoration of lung vascular barrier function as regulated by EPC expression of $\alpha_5$ integrin and fibronectin explains why the mortality was reduced when EPC expression of $\alpha_5$ integrin and fibronectin genes were silenced.

Example 15

Sepsis Induced Acute Lung injury (ALI) in Sheep

Inflammation, inappropriate neutrophil infiltration, edema, and hemorrhage are major observations seen in the lungs of septic sheep. Time course experiments have been performed in control sheep and sheep made septic who developed lung injury (Murakami, et al. (2002) *Crit. Care Med.* 30: 2083-2090). In these studies, lung lymph flow, the net pulmonary transvascular fluid filtration, and lymph-to-plasma (L/P) protein concentration ratios were measured. The product of lymph flow and L/P protein concentration ratio provides a measure of transvascular protein clearance, the permeability of the lung microvascular barrier. These studies indicated that sepsis induced a marked increase in lung microvascular permeability pulmonary edema, severe hypoxemia that was intractable to ventilation with oxygen, and an increase in the physiological shunt. Thus, studies such as this can be carried out in sheep so that the development of microvascular injury as well as the recovery phase following transplantation with syngeneic EPCs can be continuously monitored. This clinically relevant sheep model of sepsis-induced lung injury is used to evaluate whether a reduction in the increase in pulmonary vascular permeability can be achieved and whether vascular regeneration occurs upon transplantation with EPCs.

Preparation of Sheep. Twelve female sheep (body weight, 35.0±1.3 kg) are surgically prepared for study under halothane anesthesia. Arterial and venous catheters are placed in a femoral artery and vein. A thermal dilution pulmonary artery flotation catheter (Baxter Edwards Critical-Care, Irvine, Calif.) is placed into the pulmonary artery through the external jugular vein. A Silastic catheter (0.062 inch inner diameter, 0.125 inch outer diameter) is positioned in the left atrium. Post-operatively, the sheep are maintained in metabolic cages with free access to food and water for a 5-day recovery period.

The entire study period last for no more than 48 hours. All catheters are connected to pressure transducers and are flushed continuously with a heparin saline solution (3 units/mL). Ringer's lactate solution is infused at a rate of 2 mL/kg/hour for a 24-hour period before the experiment is started to ensure a steady cardiovascular status. With the animals anesthetized with ketamine, a Foley urinary retention catheter is placed in the urethra 24 hours before the bacterial challenge. At 0 hour, baseline hemodynamic data and blood samples are collected. After the measurement of baseline cardiovascular data, all animals are anesthetized with ketamine 5 mg/kg and continuous halothane anesthesia.

Bacterial Challenge. For bacterial sepsis (ALI) study, the animals are divided into three or more groups of at least twelve animals per group. For example, control animal, bacteria alone, and bacteria+EPCs. $P.\ aeruginosa$ ($2-5\times10^{11}$ colony-forming units) are suspended in 30 mL of saline. Under ketamine anesthesia, the stock solution of $P.\ aeruginosa$ is instilled into the individual lung lobes of the sheep by using a bronchoscope, e.g., 10 mL into each of the right lower lobe, middle lobe and left lower lobe. Ringer's lactate solution is infused intravenously up to 10 mL/kg/hour to prevent hemoconcentration and to maintain the filling pressure. Fluid replacement is evaluated by monitoring hematocrit and left atrial pressure before and after the bacteria challenges, and EPC treated groups. Arterial blood samples are taken for blood culture at 0, 14, 24, 36, and 48 hours. Plasma concentrations of fibrin degradation products are semiquantitatively measured at 0 and 48 hours with a latex agglutination assay kit. The study continues for 48 hours with the animals conscious. After 48 hours, animals are sedated with xylazine, anesthetized with ketamine, and sacrificed by infusion of a lethal dose of potassium chloride. Lung samples are collected to evaluate lung injury. End points include survival, neutrophil sequestration in the lung, measurements of water content (edema) in the lung, fibrin degradation assay, and examination of lung injury by histology.

EPC Preparation and Administration. Mononuclear cells (MNCs) are prepared by density gradient centrifugation as described herein. CD34$^+$ positive cells are separated using magnetic cell separation system (MACS) or FACS sorting. Initially, $5\times10^7$ (50 million) CD34$^+$ MNCs are used per animal. Higher or lower doses can be used depending upon the severity of sepsis. EPCs are resuspended in sterile PBS (5 ml) and administered through jugular vein or by retro-orbital route.

Lung Histology. To assess the efficacy of the treatment with EPCs, lung tissue is excised and inflated with 10% formalin. Fixed samples are paraffin embedded, sectioned into 5-6-μm pieces, and stained with hematoxylin and eosin. Samples are analyzed by a pathologist. Twenty-four areas of lung parenchyma at 100× magnification are graded on a scale of 0 to 4 (0, absent, appears normal; 1, light; 2, moderate; 3, strong; 4, intense) for congestion, edema, inflammation, and hemorrhage. A mean score for each of the variables is then calculated. A total histopathological score (maximum 20) is derived from the sum of the mean scores of the four variables. Additionally, levels of airway obstruction are obtained with a standardized protocol. Ten bronchi and 25 bronchioles are investigated, and the percentage of area obstructed by the cast is estimated (0-100%). Airways are classified as either bronchial or bronchiolar by using the following criteria. Bronchi are defined as airways with supporting cartilage and/or mucous glands with bronchioles lacking supporting cartilage and mucous gland structures. Bronchiolar airways include respiratory/terminal bronchioles that lack supporting stromal tissue with alveolar septa branching from the limited connective tissue underlying the airway lining epithelium. The main bronchus is excluded from the analysis because cast materials in these large airways usually are displaced during gross tissue sectioning. The results are represented by the mean percentage of the airway area obstructed by the cast.

Statistical Analysis. Data is expressed as mean±se. Two-way analysis of variance is done for multiple comparisons, and Scheffé's post hoc test is used to compare data within the groups. For the changes in hemokinetics and blood gases over time, the Student's t-test is used to compare data between the groups. In the histologic study, a nonparametric Kruskal-Wallis test is performed. A $p<0.05$ is considered statistically significant.

Example 16

Recombinant EPCs

It is contemplated that EPCs releasing eNOS-derived NO or sphingosine-1-phosphate (S1P), mediators will have an endothelial barrier protective effect through different mechanisms (Mehta & Malik (2006) *Physiol. Rev.* 86: 279-367), and be more effective in reversing increased lung microvascular permeability, edema formation, and sequestration of PMNs compared to non-transduced EPCS. The underlying premise is that EPCs transduced with either eNOS (endothelial nitric oxide synthase) or spk1 (sphingosine kinase 1) will enhance repair of the lung microvascular barrier after injury. Thus, EPCs are transduced ex vivo by electroporation, using methods well-known in the art (Zhao, et al. (2005) *Circ. Res.* 96: 442-450), which typically results in 80% efficiency of expression. Control studies involve transduction with vector only. The effects of vector-transduced EPCs and EPCs transduced with spk1 or eNOS in reversing lung microvascular injury and edema formation and lung inflammation induced by sepsis is subsequently determined. Alterations in lung vascular permeability is quantified by lung microvessel filtration coefficient ($K_{f,c}$), $^{125}$I-albumin PS product, lung extravascular water content, and lung PMN sequestration and migration. Studies are performed to determine uptake of 111-In-oxine-labeled PMNs and PMN counts in BAL in both control and EPC transplantation groups to identify the most effective cell-based therapy that reduces PMN infiltration and inflammation in lungs. These studies also determine whether a specific EPC transplantation protocol more effectively restores integrity of microvessels and reverses edema formation. Plasma levels of NO and S1P are also monitored using conventional methods for up to 14 days after transplantation of EPCS (Spiegel & Milstien (2003) *Nat. Rev. Mol. Cell Biol.* 4: 397-

407; Huang, et al. (2006) *Med. Sci. Monit.* 12: CR103-106; Roberts, et al. (2004) *Anal. Biochem.* 331: 122-129). These measurements are coupled to analysis of expression and localization of vector-transduced EPCs and eNOS- or spk1-transduced EPCs in lungs using western blot analysis and immunofluorescence. The generation of the pro-inflammatory cytokines TNF-α, IL-6, and IL-1 in plasma and BAL are also measured to address whether release of these mediators is abrogated following treatment with the transduced EPCs compared to control EPCs.

What is claimed is:

1. A method for decreasing severity of lung injury and preventing pulmonary edema in acute lung injury comprising
    culturing bone marrow derived mononuclear cells in the absence of epidermal growth factor and in the presence of vascular endothelial growth factor-121 and vascular endothelial growth factor-165;
    selecting adherent endothelial progenitor cells expressing fetal liver kinase 1 (Flk-1), CD34, $\alpha_5\beta_1$ integrin, fibronectin and von Willebrand factor; and
    administering to the pulmonary vascular bed of a subject in need of treatment the selected adherent endothelial progenitor cells, thereby decreasing severity of lung injury and preventing pulmonary edema in the subject.

2. A method for increasing survival rate in acute lung injury comprising
    culturing bone marrow derived mononuclear cells in the absence of epidermal growth factor and in the presence of vascular endothelial growth factor-121 and vascular endothelial growth factor-165;
    selecting adherent endothelial progenitor cells expressing fetal liver kinase 1 (Flk-1), CD34, $\alpha_5\beta_1$ integrin, fibronectin and von Willebrand factor; and
    administering to the pulmonary vascular bed of a subject in need of treatment the selected adherent endothelial progenitor cells, thereby increasing survival rate in the subject.

* * * * *